United States Patent
Shademan

(10) Patent No.: US 11,503,987 B2
(45) Date of Patent: Nov. 22, 2022

(54) PLENOPTIC ENDOSCOPE WITH FIBER BUNDLE

(71) Applicant: Intuitive Surgical Operations, Inc., Sunnyvale, CA (US)

(72) Inventor: Azad Shademan, Campbell, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 781 days.

(21) Appl. No.: 16/365,514

(22) Filed: Mar. 26, 2019

(65) Prior Publication Data
US 2019/0290111 A1    Sep. 26, 2019

Related U.S. Application Data

(60) Provisional application No. 62/648,060, filed on Mar. 26, 2018.

(51) Int. Cl.
*A61B 1/00* (2006.01)
*G02B 23/24* (2006.01)
(Continued)

(52) U.S. Cl.
CPC ...... *A61B 1/00193* (2013.01); *A61B 1/00165* (2013.01); *A61B 1/04* (2013.01);
(Continued)

(58) Field of Classification Search
CPC ... A61B 1/00193; A61B 1/00165; A61B 1/04; A61B 1/0676; A61B 5/0075;
(Continued)

(56) References Cited

U.S. PATENT DOCUMENTS

| 7,872,796 B2 | 1/2011 | Georgiev |
| 7,949,252 B1 | 5/2011 | Georgiev |

(Continued)

FOREIGN PATENT DOCUMENTS

EP    WO 2018033775 A1 *    2/2018    ............... A61B 1/04

OTHER PUBLICATIONS

Fatahalian K., Lecture 18: Light-Field Cameras (Plenoptic Cameras), CMU 15-869: Graphics and Imaging Architectures, 2011, 30 pages.

(Continued)

*Primary Examiner* — Aaron B Fairchild
(74) *Attorney, Agent, or Firm* — Fish & Richardson P.C.

(57) ABSTRACT

A plenoptic endoscope includes a fiber bundle with a distal end configured to receive light from a target imaging region, a sensor end disposed opposite the distal end, and a plurality of fiber optic strands each extending from the distal end to the sensor end. The plenoptic endoscope also includes an image sensor coupled to the sensor end of the fiber bundle, and a plurality of microlenses disposed between the image sensor and the sensor end of the fiber bundle, the plurality of microlens elements forming an array that receives light from one or more of the plurality of fiber optic strands of the fiber bundle and directs the light onto the image sensor. The plurality of microlens elements and the image sensor together form a plenoptic camera configured to capture information about a light field emanating from the target imaging region.

18 Claims, 9 Drawing Sheets

(51) Int. Cl.
*H04N 5/225* (2006.01)
*A61B 1/06* (2006.01)
*A61B 1/04* (2006.01)
*A61B 5/00* (2006.01)
*G02B 13/00* (2006.01)

(52) U.S. Cl.
CPC ........ A61B 1/0676 (2013.01); G02B 23/2469 (2013.01); H04N 5/22541 (2018.08); *A61B 5/0075* (2013.01); *G02B 13/0015* (2013.01); *G02B 23/2484* (2013.01)

(58) Field of Classification Search
CPC ............ A61B 1/00006; A61B 1/00009; A61B 1/00045; A61B 1/00096; A61B 1/0016; A61B 1/00167; A61B 1/00186; A61B 1/00188; A61B 1/008; A61B 1/042; A61B 1/07; A61B 1/0075; G02B 23/2469; G02B 13/0015; G02B 23/2484; G02B 23/26; G02B 27/0075; H04N 5/22541; H04N 2005/2255; G06T 7/557
See application file for complete search history.

(56) References Cited

U.S. PATENT DOCUMENTS

| | | |
|---|---|---|
| 7,962,033 B2 | 6/2011 | Georgiev et al. |
| 2014/0206979 A1 | 7/2014 | Berkner et al. |
| 2014/0378846 A1* | 12/2014 | Hosoda ................ A61B 1/3137 600/478 |
| 2015/0145966 A1 | 5/2015 | Krieger et al. |
| 2017/0332880 A1* | 11/2017 | Ito ...................... A61B 1/00009 |
| 2018/0344130 A1* | 12/2018 | Gmeiner ............ A61B 1/00188 |
| 2019/0223704 A1 | 7/2019 | Chen et al. |

OTHER PUBLICATIONS

Georgiev T., et al., "Focused Plenoptic Camera and Rendering," Journal of Electronic Imaging, Apr. 2010, vol. 19 (2), pp. 021106-1-021106-11.
Kwan E., et al., "Development of a Light Field Laparoscope for Depth Reconstruction," Imaging and Applied Optics, 2017, 3 pages.
Le H.N.D., et al., "3-D Endoscopic Imaging using Plenoptic Camera," Conference on Lasers and Electro-optics, 2016, 2 pages.
Le H.N.D., et al.. "Experimental Assessment of a 3-D Plenoptic Endoscopic Imaging System," Chinese Optics Letters, May 2017, vol. 15 (5), pp. 051701-1-051701-5.
Ng R., et al., "Light Field Photography with a Hand-held Plenoptic Camera," Stanford Tech Report CTSR, 2005, pp. 1-11.
Shademan A., et al., "Plenoptic Cameras in Surgical Robotics: Calibration, Registration and Evaluation," IEEE International Conference on Robotics and Automation (ICRA), 2016, 7 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

PLENOPTIC ENDOSCOPE WITH FIBER BUNDLE

PRIORITY CLAIM

This application claims priority to U.S. Provisional Application 62/648,060, filed on Mar. 26, 2018, the entire contents of which are incorporated herein by reference.

BACKGROUND

Plenoptic cameras (sometimes referred to more generally as light field cameras), capture information on a light field emanating from an object or surface with a lens and image sensor configuration that captures information on both the intensity and the direction of light. A plenoptic endoscope facilitates light field imaging of an object or surface inside the human body.

SUMMARY

In one aspect, the present disclosure features a plenoptic endoscope including a fiber bundle with a distal end configured to receive light from a target imaging region, a sensor end disposed opposite the distal end, and a plurality of fiber optic strands each extending from the distal end to the sensor end. The plenoptic endoscope also includes an image sensor coupled to the sensor end of the fiber bundle, and a plurality of microlenses disposed between the image sensor and the sensor end of the fiber bundle. The plurality of microlens elements form an array that receives light from one or more of the plurality of fiber optic strands of the fiber bundle and directs the light onto the image sensor. The plurality of microlens elements and the image sensor together form a plenoptic camera configured to capture information about a light field emanating from the target imaging region.

In some instances, the plenoptic endoscope includes a main lens assembly arranged at the distal end of the fiber bundle, the main lens arranged to direct light from the target imaging region through the plurality of fiber optic strands.

In some instances, the main lens assembly includes an objective lens defining a field of view of the light directed through the plurality of fiber optic strands.

In some instances, the fiber bundle is flexible. In some instances, the fiber bundle is configured to be inserted into an animal or human body.

In some instances, the fiber bundle includes a proximal portion and a distal portion coupled at a joint along a length of the fiber bundle, the joint enabling angular movement of the distal portion with respect to the proximal portion about the joint. In some instances, the joint includes an electric motor configured to cause the angular movement of the distal portion with respect to the proximal portion about the joint.

In some instances, the fiber bundle includes a plurality of separate, individually flexible arms, each of the plurality of arms includes a subset of the plurality of fiber optic strands. In some instances, the image sensor includes a plurality of image sensing regions, and each image sensing region is arranged to receive light from one of the plurality of separate individual flexible arms. In some instances, a first image sensing region of the plurality of image sensing regions is configured to sense at least a first wavelength of light, and a second image sensing region is configured to sense at least a second wavelength of light that is not sensed by the first image sensing region. In some instances, the first image sensing region is configured to sense at least visible light, and the second image sensing region is configured to sense at least infrared light.

In some instances, the plenoptic endoscope includes at least one light source and a subset of the plurality of fiber optic strands of each flexible arm forms a light guide arranged to direct light from the light source to the distal end of each flexible arm to illuminate at least a portion of the target imaging region. The distal end of a first flexible arm is configured to direct light of at least a first wavelength of light and the distal end of a second flexible arm is configured to direct light of at least a second wavelength of light that is not directed by the first flexible arm. In some instances, the image sensor includes a plurality of image sensors, where each image sensor is arranged to receive light from one of the plurality of separate individual flexible arms.

In some instances, the plenoptic includes a light source, and a subset of the plurality of fiber optic strands forms a light guide arranged to direct light from the light source to the distal end of the fiber bundle to illuminate the target imaging region.

In some instances, each of the plurality of microlens elements is arranged to receive light from one or more of the plurality of fiber optic strands of the fiber bundle and to direct the light onto the image sensor.

In some instances, one or more of the plurality of microlens elements is arranged to receive light from one of the plurality of fiber optic strands of the fiber bundle and direct the light onto the image sensor.

In some instances, the plenoptic endoscope includes one or more processing devices operatively coupled with the image sensor and configured to calculate surface image data for a surface in the target imaging region. In some instances, the one or more processing devices is configured to generate representations of a depth map based on the surface image data and a photographic image.

In another aspect, this document features a method of presenting an image on a display of a plenoptic endoscope. The method includes receiving, at an image sensor, light from a target imaging region, where the light is captured using a plurality of microlens elements disposed at a sensor end of a fiber bundle including a plurality of fiber optic strands, and the plurality of microlens elements and the image sensor together form a plenoptic camera to capture both intensity and direction information of the light. The method includes computing, based on an output of the image sensor, a representation of a portion of the target imaging region, computing, based on the output of the image sensor, a depth map associated with the portion of the target imaging region, and presenting the image on the display of the plenoptic endoscope, the image being generated from the representation of the portion and the associated depth map associated with the surface. In some instances, the image is a multi-focus image.

DESCRIPTION OF DRAWINGS

Like reference symbols in the various drawings indicate like elements.

DETAILED DESCRIPTION

Figure 1A:
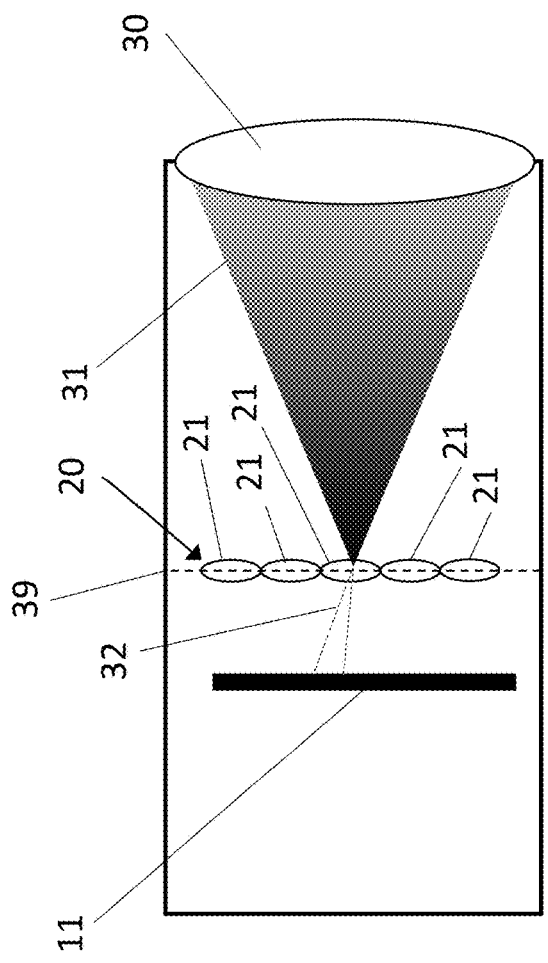
FIGS. 1A and 1B are schematics of two different types of plenoptic imaging systems configured to be used in a plenoptic endoscope.

This document describes a plenoptic endoscope that combines an endoscope having a fiber bundle configured to be inserted into a body and relaying images of areas therein with a plenoptic camera system. The plenoptic camera system captures direction and intensity information about the light received via the fiber bundle to create a three-dimensional depth map of the imaged structures and surfaces viewed by the endoscope. Aspects of the plenoptic endoscopes disclosed herein enable generation of quantitative information regarding the size and position of internal structures, which in turn may aid the operation of surgical instruments (e.g., that in a telesurgical system), operating in the view of the plenoptic endoscope. For example, a plenoptic endoscope imaging a target structure and a tool can calculate the spatial relationship (e.g., distance and orientation) between the tool and the target structure in order to guide the tool's interaction with the target structure.

Plenoptic cameras (sometimes referred to more generally as light field cameras), capture light emanating from an object or surface with a lens and image sensor configuration that captures both the intensity and direction of the light. The light field associated with the captured light can then be resolved from the information captured by the image sensor. A plenoptic endoscope utilizes such light field photography techniques, for example, to generate a three-dimensional (3D) and/or spectral image of an object or surface (e.g., inside the human body). Plenoptic cameras can be of different types. A standard plenoptic camera includes an array of multiple microlenses placed one focal length away from the image plane of a sensor. A focused plenoptic camera includes a microlens array in front of, or behind the focal plane of the main lens, and the light field is sampled in a way that trades angular resolution for higher spatial resolution. In a focused plenoptic camera, images can be post focused with a much higher spatial resolution than with images from the standard plenoptic camera.

A plenoptic endoscope is an endoscopic imaging system that includes a plenoptic camera. The imaging system may include relay optics at the terminal end of an endoscope arranged to form an image of the surface or object being investigated. In some implementations, the plenoptic camera includes an image sensor (e.g., a CCD or CMOS digital camera sensor), and a microlens array positioned at a location between the image sensor and the imaging system. Based on the known optical characteristics of the microlens array and the positioning with respect to the image sensor, light received by the image sensor from the relay optics is deconstructed in a light field that includes depth information from each imaged surface with respect to the relay optics. In this manner, a 3D image or depth map of the surface of object can be created from the captured light field information.

In robotic surgery, visualization and perception of the surgical site is an important aspect, and quantitative imaging (e.g., a depth map or 3D image) can improve surgical outcome by providing meaningful additional information to the surgeon. Several technologies are currently available for quantitative 3D imaging in the operating room, such as magnetic resonance imaging (MRI), computed tomography (CT) scans, and 3D ultrasound. However, these are often difficult to integrate into real-time surgery. One solution is to use stereo endoscopic images to generate 3D models, and to reconstruct and track surfaces of soft tissue using such 3D models. Since surgeons already use stereoscopic endoscopes for depth perception during minimally invasive surgery (MIS), the hardware is already available. However, such quantitative imaging entails calibration of endoscopes and stereo matching, which may be challenging in some cases. In some cases, plenoptic endoscopes can be used to generate a 3D visualization by leveraging the light field photography techniques used in such endoscopes. In addition to creating a 3D depth map of the field, plenoptic systems can provide a focused image at different depths; this is not something a stereo camera could do.

A representative example of a plenoptic endoscope includes a plenoptic imaging system integrated with an endoscope constructed from a bundle of optical fiber strands. The bundle of optical fiber strands (hereinafter referred to simply as a 'fiber bundle') is used both as a light guide to illuminate a target imaging region, and to transmit the light emanating from the target imaging area, from a distal end (e.g., the end positioned at the imaging region inside the body) to a sensor end (e.g., the end transmitting the light from the fiber bundle to the imaging system) of the endoscope. In some instances, a group of the fiber optic strands are used for illumination, while a different group of the fiber optic strands are used for relaying the light from the target imaging region end to the plenoptic camera. The plenoptic endoscope includes an array of microlenses between the sensor end of the fiber bundle and an image sensor of the imaging system. In some examples, a second array of microlenses is arranged on the distal end of the fiber bundle to focus the incoming light into the fiber bundle. In some implementations, a series of microlenses of appropriate powers may be used in place of a single microlens. In some examples, a relay lens assembly is also provided at the distal end of the fiber bundle to define the field of view of the light received by the second array of microlenses. With this plenoptic endoscope arrangement, a calibration algorithm can be developed, based on, for example, the relative positioning of the image sensor and the microlenses, and their optical characteristics, to convert the data received by the image sensor into a 2D image and/or a 3D depth map of the view of the plenoptic endoscope.

Certain aspects of the plenoptic endoscope embodiments provide a number of advantages over existing systems. In some implementations, by providing flexible fiber optic strands in the fiber bundle, that the technology described herein enables construction of a flexible fiber bundle for use in an endoscope. The flexible fiber bundle can include both (i) light field fibers carrying a light from an imaging region to a plenoptic camera and, (ii) light guide fibers carrying illumination into the imaging region packaged together as a single flexible unit. In some implementations, the flexible plenoptic endoscope described herein may be used for 3D depth sensing and surface reconstruction in endoluminal surgery/interventions at portions of the human body that are challenging to reach with rigid endoscopes.

In some implementations, a plenoptic endoscope includes a wristed or articulated fiber bundle with 3D depth sensing and surface reconstruction capabilities. In this example, the fiber bundle is coupled to a mechanized wristed endoscope tip with 3D depth sensing and surface reconstruction capabilities. Flexibility of the fiber bundle allows the fiber bundle to bend with the articulation of the mechanized wrist, thereby potentially facilitating an enhanced field of view as compared to a non-wristed endoscope.

In some implementations, a plenoptic endoscope includes a bifurcated fiber bundle with 3D depth sensing and surface reconstruction capabilities. In such implementations, the fiber bundle is bifurcated into two or more separate subsets of fiber bundles, each potentially imaging/mapping a different portion of the surgical site. In some instances, the bifurcated plenoptic endoscope may enable an extended field of view and/or enable a user to look sideways or backwards depending on the dexterity of each distal section of the bifurcated fiber bundle.

Figure 1B:
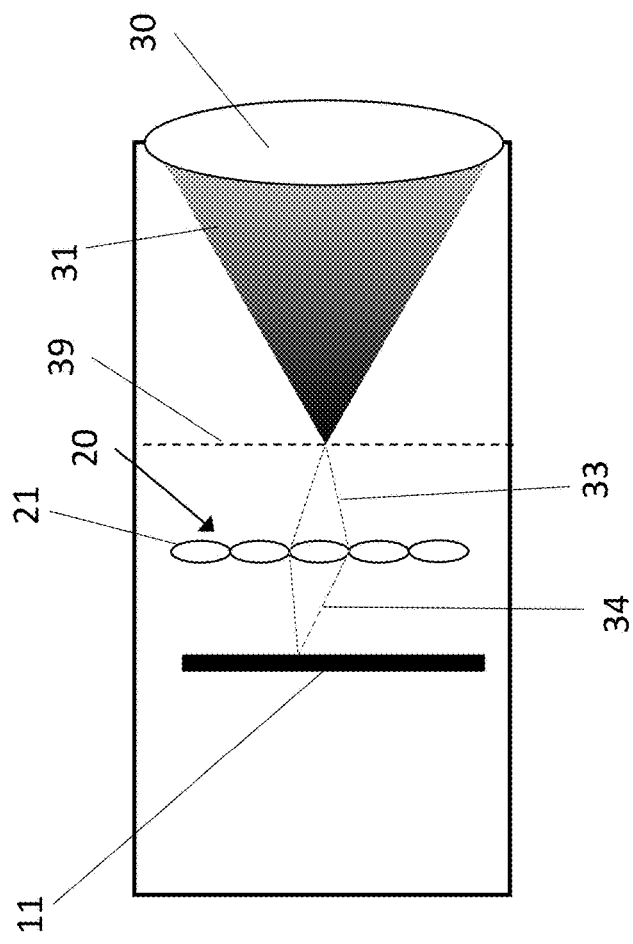

FIGS. 1A and 1B are schematics of two different types of plenoptic imaging systems. FIG. 1A shows a plenoptic camera that includes an objective lens 30, an image sensor 11, and a microlens array 20 arranged between the image sensor 11 and the objective lens 30. The microlens array 20 includes individual microlenses 21 forming a 2D matrix. FIG. 1A represents a standard plenoptic system, where the objective lens 30 has a fixed focal plane 39 on which the microlens array 20 is arranged. In operation, the objective lens 30 directs light along a cone 31 to the focal plane 39 and each microlens 21 projects a sampling 32 of a corresponding cone 31 onto a portion of the image sensor 11. The multiple microlenses together allow for capturing images of the same object as if viewed from different directions. As a result of the different spatial relationship between each microlens 21 and the objective lens 30, the image data captured by the image sensor 11 is able to sense multiple spatially-shifted views of the target imaging region, and thereby capture information regarding the depth of the source of the light rays directed from the objective lens 30 to the image sensor 11. FIG. 1B shows an alternative plenoptic camera 10 configuration, whereby the microlens array 20 is positioned between the fixed focal plane 39 of the objective lens 30 and the image sensor 11, such that the portion of light 33 captured by each microlens 21 is defocused, and each microlens 21 projects a focused light field 34 onto the image sensor 11. More details about plenoptic cameras may be found in the reference "Light Field Photography with a Hand-held Plenoptic Camera," Stanford Tech Report CTSR 2005-02, the entire content of which is incorporated herein by reference.

Figure 2:
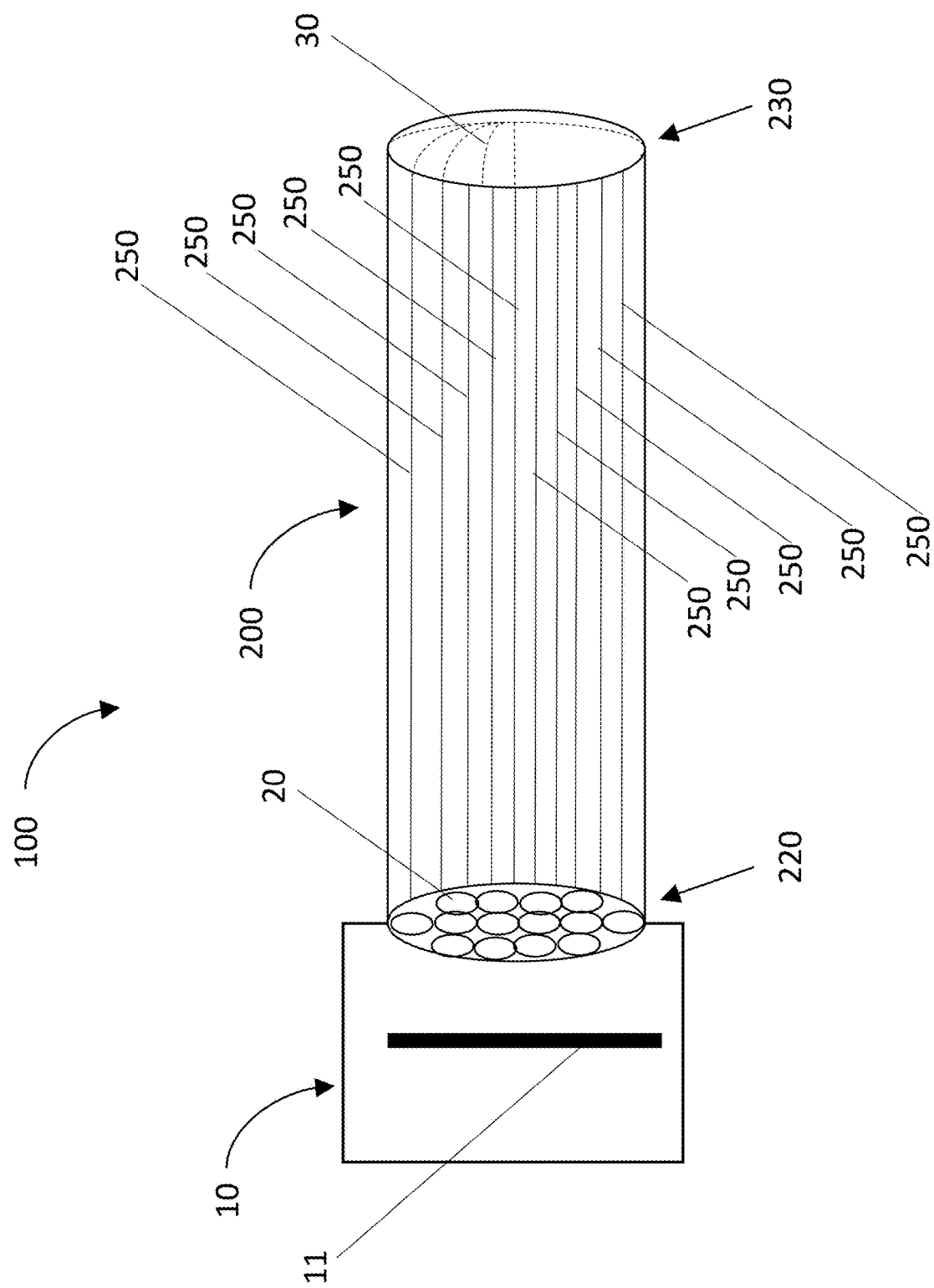
FIG. 2 is a schematic diagram of an example of a plenoptic endoscope with a fiber bundle.

FIG. 2 is a schematic diagram of an example of a plenoptic endoscope 100 with a fiber bundle 200. The plenoptic endoscope 100 includes a plenoptic camera system 10 operatively coupled to the fiber bundle 200 at a sensor end 220 of the fiber bundle 200. An objective lens 30 is disposed at an opposite, distal end 230 of the fiber bundle 200 to capture light from a target imaging region into the fiber bundle 200. In operation, the fiber bundle transmits the light received through the objective lens 30 to the image sensor 11 of the plenoptic camera system 10. In some instances, the plenoptic camera system 10 is either a standard plenoptic arrangement 104 or a focused plenoptic arrangement 105. The fiber bundle 200 is constructed from a plurality of fiber optic strands 250, which are grouped to create a pathway for light to travel to between the distal end 230 and the sensor end 220. A microlens array 20 is arranged at the sensor end 220 of the fiber bundle 200. This microlens array 20 is positioned with respect to the image sensor 11 of the plenoptic camera system 10 to enable the image sensor to resolve the light field associated with the light captured by the objective lens 30 and transmitted through the fiber bundle 200. In some instances, the fiber bundle 200 includes a second microlens array 320 (shown in FIG. 3) between the objective lens 30 and the fiber optic strands at the distal end 230. In some instances, a portion of the fiber bundle 200 is flexible, and another portion of the fiber bundle is substantially rigid.

In operation, the plenoptic endoscope 100 is used to image anatomy inside a human or animal body, by inserting the distal end 230 of the fiber bundle 200 into the body and relaying light captured by the objective lens 30 at the distal end 230 to the plenoptic camera system 10 at the sensor end 220. In this configuration, the plenoptic endoscope 100 enables generation of both a photographic image based on the view of the objective lens 30, which can be re-focused at different depths, as well as a depth map of the surfaces and structures visible in the field of view. In some implementations, the plenoptic endoscope 100 may be used outside the body as well. In some instances, and especially for uses inside a body, the fiber bundle 200 also includes one or more fibers acting as a light guide to direct light from a source outside the body to the distal end 230 to provide illumination to the anatomy or surfaces being imaged. In some example, the fiber bundle 200 is sealed inside an outer casing (not illustrated) to enable safe insertion of the distal end 230 of the fiber bundle 200 into an animal or human body.

Figure 3:
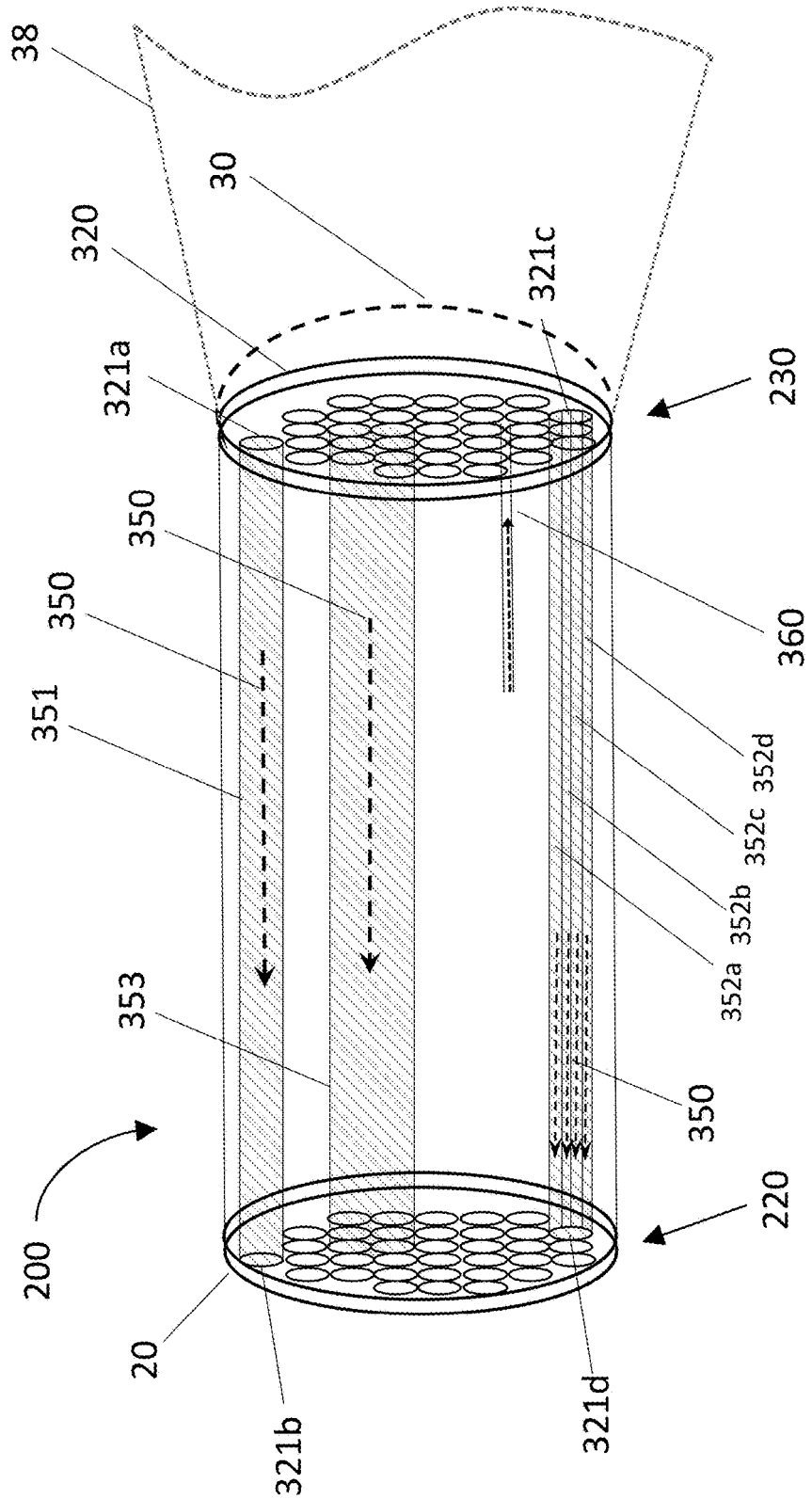
FIG. 3 is a schematic diagram of the internal structure of a fiber bundle of the plenoptic endoscope of FIG. 2.

FIG. 3 is a schematic diagram of the internal structure of a fiber bundle of the plenoptic endoscope 100 of FIG. 2. In FIG. 3, the fiber bundle 200 includes an objective lens 30 at the distal end 230, which defines a field of view 38 from which light is directed by the objective lens 30 to the image sensor 11 of the plenoptic camera system 10 via the fiber bundle 200. As detailed above with respect to FIG. 2, the fiber bundle 200 includes a plurality of fiber optic strands 250 spanning the length of the fiber bundle 200. However, multiple configurations are possible, and three exemplary arrangements are depicted in FIG. 3. The fiber bundle 200 includes a microlens array 320 at the distal end 230 and a microlens array 20 at the sensor end 220. In some implementations, the fiber optic strands 250 span the length of the fiber bundle 200 between the two microlens arrays 20, 320. In a first configuration, each individual fiber optic strand 351 is arranged with respect to the microlens arrays 20, 320 such that a single microlens 321a at the distal end 230 is optically coupled to a single fiber optic strand 351 and, similarly, a single microlens 321b at the sensor end 220 is optically coupled to the same single fiber optic strand 351. In this first configuration, light received by each microlens 321a at the distal end 230 is directed (as illustrated by arrow 350) to a corresponding microlens 321b at the sensor end 220 by the single fiber optic strand 351.

In a second configuration, a fiber optic strand 353 is arranged with respect to the microlens arrays 20, 320 such that a group of microlenses at the distal end 230 are optically coupled to a fiber optic strand 353 and, similarly, a group of microlenses at the sensor end 220 are optically coupled to the same fiber optic strand 353. In this second configuration, light received by a group of microlenses at the distal end 230 is directed (as illustrated by arrow 350) to a corresponding group of microlenses at the sensor end 220.

In a third configuration, a group of fiber optic strands 352a-352d are arranged with respect to the microlens arrays 20 such that a single microlens 321c at the distal end 230 is optically coupled to the group of fiber optic strands 352a-352d and, similarly, a single microlens 321d at the sensor end 220 is optically coupled to the same group of fiber optic strands 352a-352d. In this third configuration, light received by each microlens 321c at the distal end 230 is directed (as illustrated by arrow 350) to a corresponding microlens 321d at the sensor end 220 by the group of fiber optic strands 352a-d. A fiber bundle 200 may be constructed from any combination of the different fiber optic strand configurations.

Continuing to refer to FIG. 3, the fiber bundle 200 includes one or more fiber optic strands configured as illumination fibers 360 (e.g., light guides) to transmit light from a source of illumination (not illustrated) to the region within the field of view 38 of the objective lens 30. In some instances, the illumination fibers 360 are positioned between the light sensing fibers (e.g., fiber optic strands 351, 352a-352b, 353) carrying sensed light to the plenoptic camera system 10. In some instances, the light guides exit the fiber bundle 200 at the distal end 230 in small gaps between each microlens 21 of the microlens array 20. A distribution of the illumination fibers 360 among the illumination fibers can be adjusted to minimize effects of specular light in the field of view 38 of the endoscope. In some instances, the illumination fibers 360 achieve an even distribution of light at the surgical site, for example by distributing them circumferentially around the light sensing fibers. The illumination fibers 360 can be dynamically controlled to adjust the lighting in the field of view 38 to create images with more uniform illumination. As an example, if the right side of the image is closer to the objective lens 30, less illumination might be required for that area, compared to the left side of the image, which has a greater distance from the objective lens 30. In other instances, the illumination fibers 360 are positioned outside of the light sensing fibers.

Figure 4:
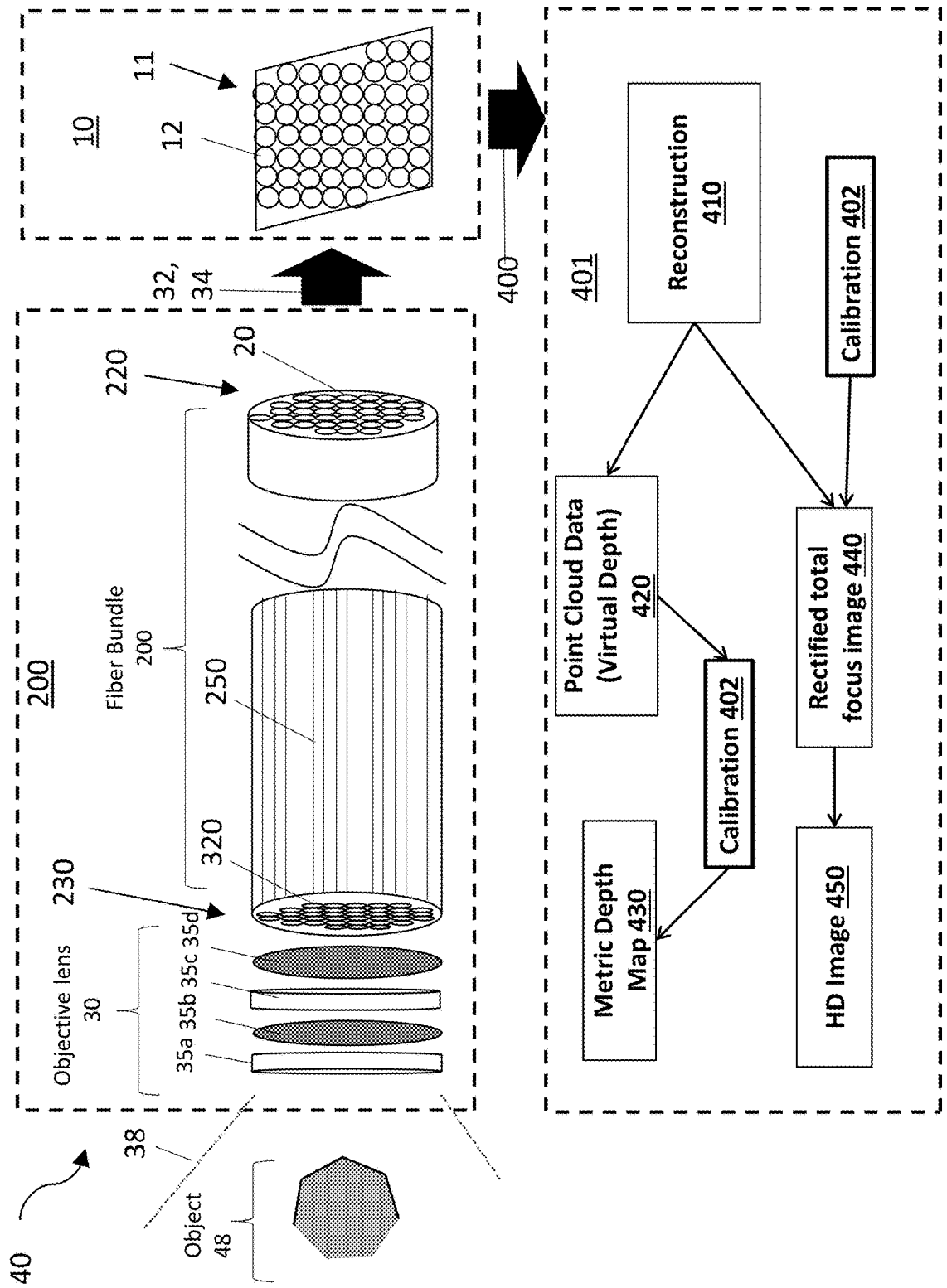
FIG. 4 is a block diagram of an example of a plenoptic endoscope and subsequent image processing steps performed on images captured using the plenoptic endoscope.

FIG. 4 is a block diagram of an example of a plenoptic endoscope system 40 and subsequent image processing steps. The plenoptic endoscope system 40 includes a fiber bundle 200 attached to a plenoptic camera system 10 and an image processor 401. In some instances, the objective lens 30 of the fiber bundle 200 includes a set of relay lenses 35a-35d (35, in general) positioned between beyond the microlens array 20 at the distal end 230 of the fiber bundle 200 to extend the distance between the objective lens 30 and the microlens array 320. In some instances, the objective lens 30 is positioned at the distal end 230 without a set of relay lenses 35, and in other instances, the microlens array 320 at the distal end 230 is configured to operate as an objective lens. In some instances, the relay lenses 35 enable other optical changes of the light transmitted to the fiber bundle 200, such as changing the focal length by changing the field of view 38. A number of optical configurations can be used to deliver light from an object 48 positioned within a field of view 38 to the fiber optic strands 250, which in turn deliver the light to the microlens array 20 at the sensor end 220. From the microlenses array 20 at the sensor end 220, a defocused or focused image is projected from each microlens 21 onto the image sensor 11 of the plenoptic camera system 10. The image sensor 11, in some instances, is an array of photosensitive pixels 12. The image sensor 11 generates image data 400 that is passed onto to a processor 401. The input to the processor 401 are images obtained from the light field in relation to each microlens 21. The first step, reconstruction 410, is to match local intensity in nearby image regions (microlens array sub-images). Once common image features, for example, corners, which correspond to the same physical object, are identified, the pixels are back projected onto the light field (multi-image triangulation) to reconstruct a local 3D point cloud 420. The local 3D point cloud 420 from nearby microlens array 320 sub-images overlap, from which the common areas are removed. The result is a reconstructed 3D surface 430 of the object 48 that can be projected on to a total focus image 440 to create a regular image 450. In some implementations, the foregoing process may be calibrated tin accordance with a cost function associated with the above-referenced back-projection. For example, the cost function can be a function of distances between lenses in the microlens array 320, the distance of the microlens array 320 to the distal end 230 of the fiber bundle 200, and/or the distance of the microlens array 320 to image sensor 11. In addition, for a metric point cloud, the intrinsic parameters of each microlens 21, for example, focal length, is calculated.

Figure 5:
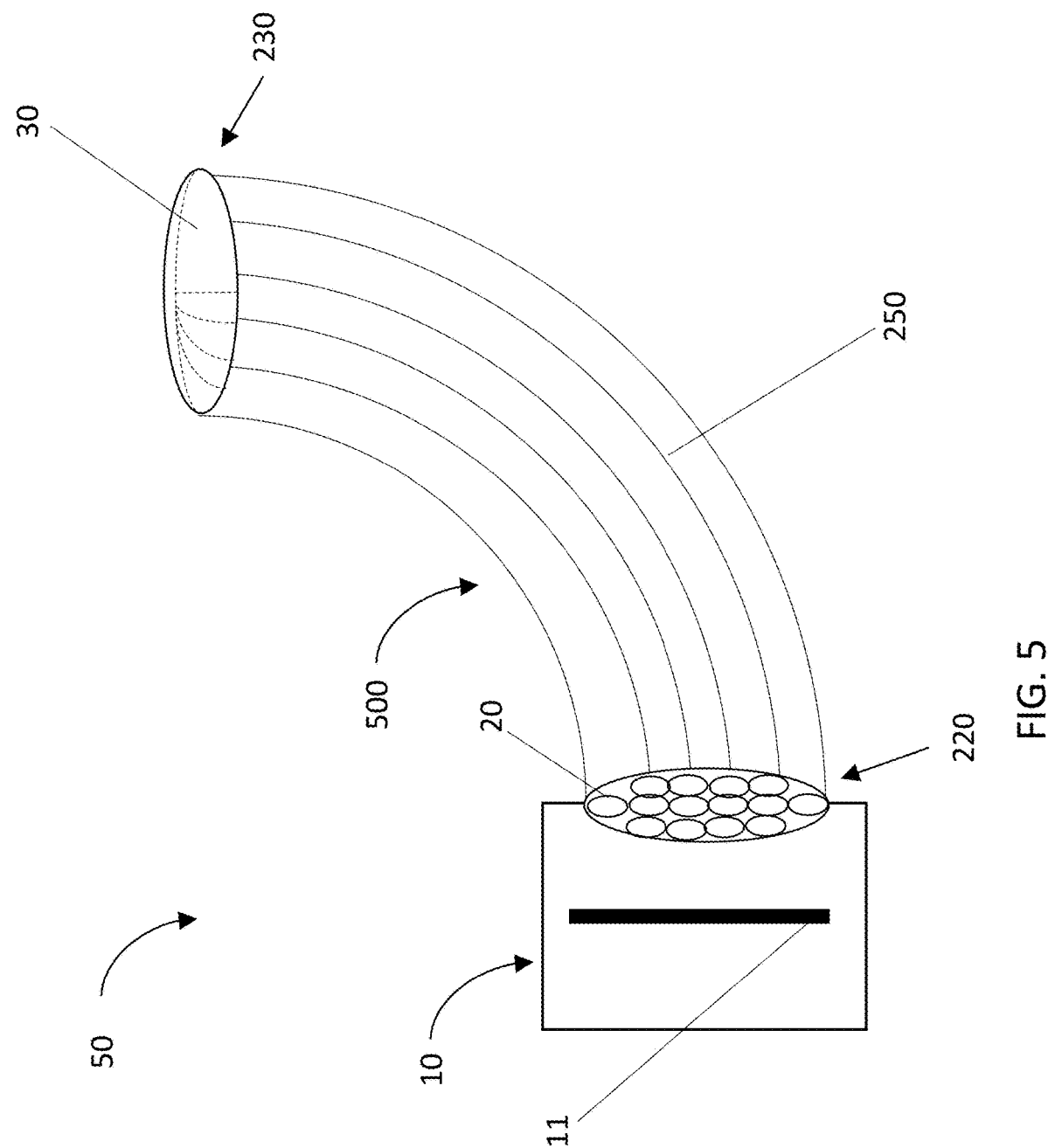
FIG. 5 is a schematic diagram of an example of a plenoptic endoscope with a flexible fiber bundle.

FIG. 5 is a schematic diagram of an example of a plenoptic endoscope 50 with a flexible fiber bundle 500. The plenoptic endoscope 50 includes a plenoptic camera system 10 with the flexible fiber bundle 500 arranged to direct light captured by an objective lens 30 at a distal end 230 of the flexible fiber bundle 500 to an image sensor 11 of the plenoptic camera system 10. The flexible fiber bundle 500 includes a first microlens array 20 at a sensor end 220 and, in some instances, a second microlens array (as shown in FIG. 3) at the distal end 230. Because individual fiber optic strands 250 are able to flex and bend, the flexible fiber bundle 500 is constructed to allow the flexibility of the fiber optic strands 250 to permit flexion of the entire flexible fiber bundle 500 as illustrated. In operation, the flexible fiber bundle 500 enables the plenoptic camera system 10 to remain stationary while the objective lens 30 is oriented in an arbitrary position. In each arbitrary position of the flexible fiber bundle 500, the distance between the first and second microlens arrays is approximately equal due to the reluctance of the individual fiber optic strands 250 to compress or stretch significantly. As a result, a precise distance between each microlens 21, as provided by the calibration process, can be maintained. FIG. 5 is only an example illustration of a bend in a flexible fiber bundle 500, and any apparent change in the length of the fiber optic strands 250 shown is not intended to reflect any real material properties.

Figure 6:
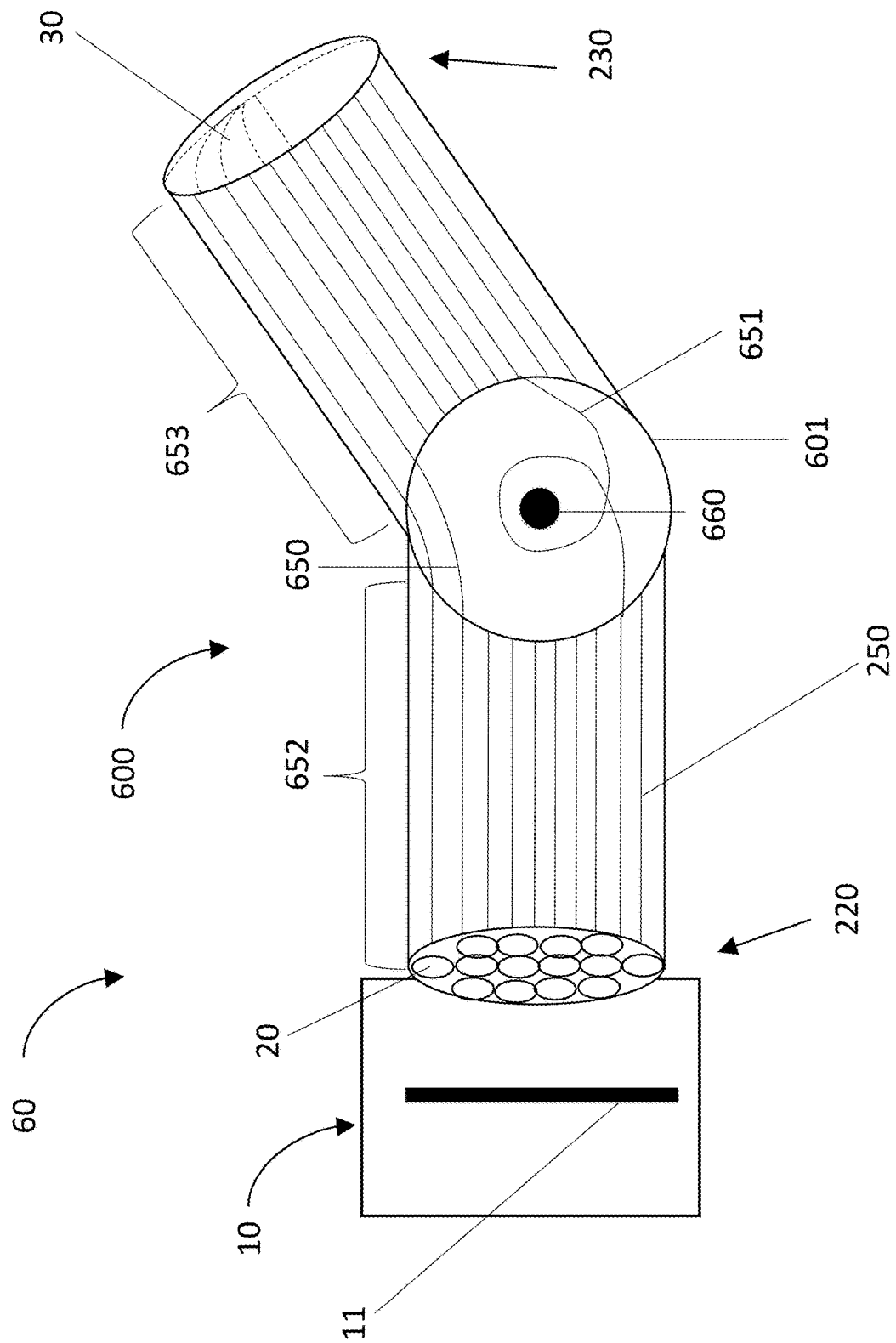
FIG. 6 is a schematic diagram of an example of a plenoptic endoscope with a fiber bundle having an articulated joint in the fiber bundle.

FIG. 6 is a schematic diagram of an example of a plenoptic endoscope 60 with an articulated fiber bundle 600 having a joint 601 disposed along the length of the articulated fiber bundle 600, the joint coupling a proximal portion 652 of the fiber bundle to a distal portion 653 of the fiber bundle. The plenoptic endoscope 60 includes a plenoptic camera system 10 with the articulated fiber bundle 600 arranged to direct light from an objective lens 30 at a distal end 230 of the articulated fiber bundle 600 to an image sensor 11 of the plenoptic camera system 10. The articulated fiber bundle 600 includes a first microlens array 20 at a sensor end 220 and, in some instances, a second microlens array (as shown in FIG. 3) at the distal end 230. Because individual fiber optic strands 250 are able to flex and bend, the articulated fiber bundle 600 is constructed to allow the flexibility of the fiber optic strands 250 to permit a joint 601 to bend the articulated fiber optic bundle 600 as illustrated. In operation, the articulated fiber bundle 600 enables the plenoptic camera system 10 to remain stationary while the distal portion 653 of the fiber bundle is oriented at an angle within a range of angles as afforded by the movement of the distal portion 653 of the fiber bundle 600 with respect to the proximal portion 652 of the fiber bundle 600 around the joint 601. In some instances, the joint 601 includes a motor 660 controlling the position of the distal portion 653 of the fiber bundle 600 with respect to the proximal portion 652 of the fiber bundle 600. In some instances, the fiber optic strands 250 bend (as indicated at point 650) as they pass through the joint 601. In some instances, the joint 601 is articulated via a cable mechanism around the fiber bundle 600. In some instances, the joint 601 is articulated via a cable mechanism (not shown) similar to other wristed instruments, for example a vessel sealer. In some instances, the fiber optic strands are spooled (as indicated by loop 651) or are otherwise bunched near the joint 601 such that the joint's 601 articulation of the articulated fiber bundle 600 maintains an approximately equal distance between the first and second microlens arrays along each of the individual fiber optic strands 250. Any spooling mechanism can be configured in accordance with any curvature limitations associated with the fibers.

Figure 7:
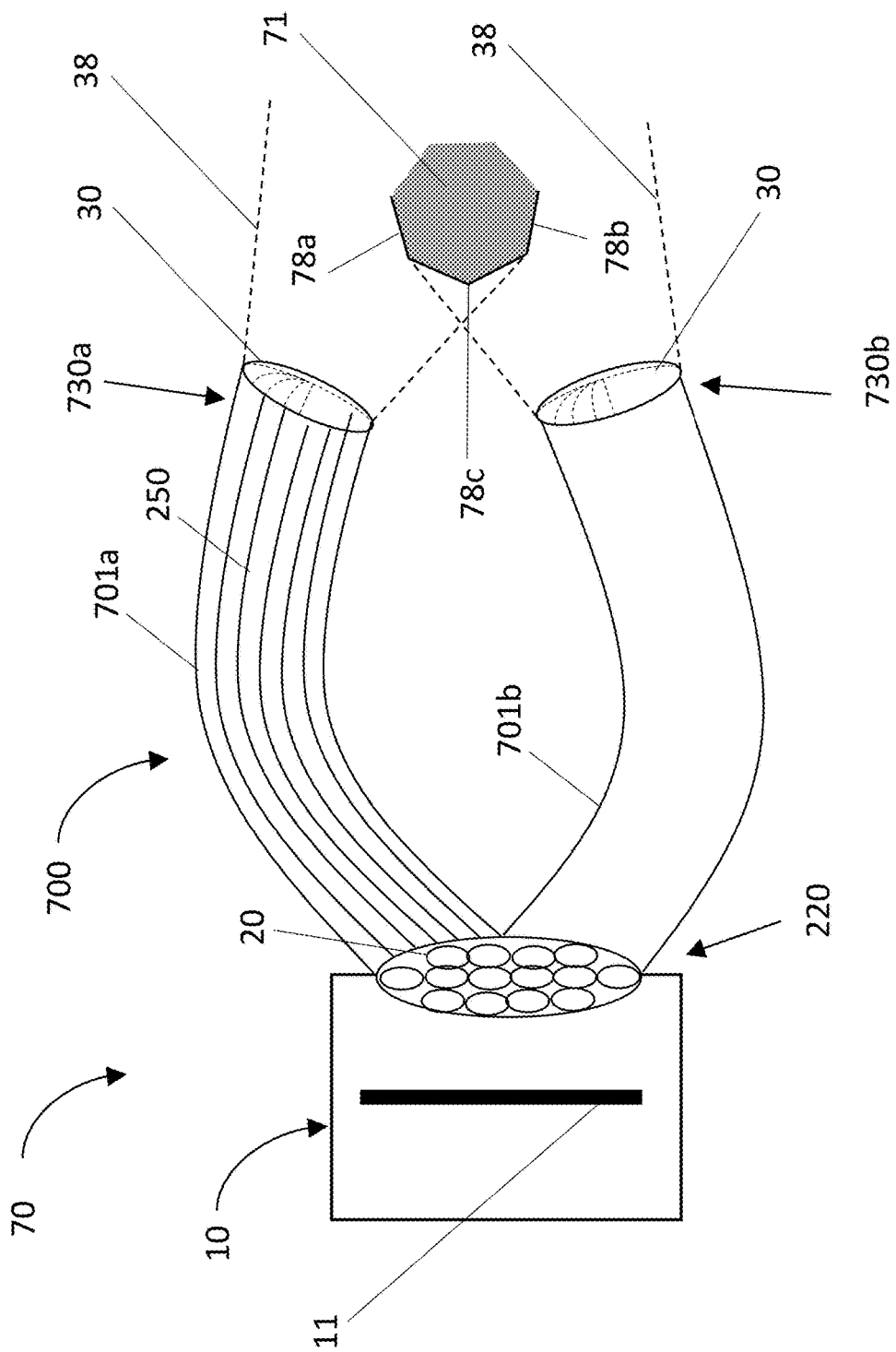
FIG. 7 is a schematic diagram of an example of a plenoptic endoscope with a bifurcated fiber bundle.

FIG. 7 is a schematic diagram of an example of a plenoptic endoscope 70 with a bifurcated fiber bundle 700. The plenoptic endoscope 70 includes a plenoptic camera system 10 with the bifurcated fiber bundle 700 arranged to direct light from two objective lenses 30 at separate distal ends 730a, 730b of the bifurcated fiber bundle 700 to an image sensor 11 of the plenoptic camera system 10. The bifurcated fiber bundle 700 disposed at the distal end of the endoscope includes a single microlens array 20 at a sensor end 220 and, in some instances, a second microlens array (as shown in FIG. 3) at each of the distal ends 730a, 730b. In some instances, the bifurcation refers to one subset of fiber strands forming a first arm, and a different subset of fiber strands forming a second arm. In some implementations, the bifurcated fiber bundle 700 can include a set of fiber optic strands 250 bifurcated into two separate fiber bundles 701a, 702b, with each having a distal end 730a (or 730b) with an objective lens 30. In some implementations, the light from different fiber bundles may be sensed using different combinations of sensors and/or filter. For example, appropriate optical filters can be used with one fiber bundle 701a for sensing visible light, whereas emission filters can be used with another fiber bundle 701b for sensing infrared light. This in turn can enable, for example, overlaying information about a tumor (e.g., as captured in the infrared range using the fiber bundle 701b) onto a visible light image (e.g., as captured in the visible range using the fiber bundle 701b). In some instances, the two separate fiber bundles 701a, 702b are coupled to separate image sensors (not shown), where the separate image sensors are configured to be responsive to at least partially non-overlapping frequency ranges.

In operation, the bifurcated fiber bundle 700 enables the plenoptic camera system 10 to remain stationary while each of the objective lens 30 are oriented in different positions. In some instances, the two objective lenses 30 may be oriented to view the same object 71, and, as shown, but from different viewpoints, for example to overlay anatomy reconstructed from one view onto anatomy reconstructed on the other view. For example, each objective lens may be oriented to observe a different surface 78a, 78b of the object 71 in their respective fields of view 38. In some cases, the respective fields of view of the two objective lenses may be at least partially overlapping. For example, a portion of the surface 78c may be within the field of view 38 of both objective lenses of the bifurcated fiber bundle 700. Therefore, in some implementations, the bifurcated fiber bundle 700 may enable (1) a larger field of view for viewing an object 71, and/or (2) calculation of a correlation between overlapping portions of the two fields of view 38. In some instances, the correlation is used to create a depth map of the surface 78a, 78b, 78c of the object 71. In some instances, because the overlapped surface 78c is viewed by two objective lensed, a high spatial resolution depth mapping of the surface 78c is possible. Further, the bifurcated endoscope may be used to enable different viewing directions (e.g., sideways, backwards etc.) depending, for example, on the dexterity of each distal arm of the bifurcated fiber bundle.

While the description herein specifically mentions a bifurcated fiber bundle with two branches or arms, more branches or arms are also within the scope of this disclosure. For example, three or more flexible arms, each including a separate subset of the fiber bundle, can be implemented suing the technology described herein. In some implementations, one of the subsets of the fiber bundle may be used for transmitting light from a light source, and one or more of other subsets of the fiber bundle may be used to transmit captured light back to the image sensor.

Figure 8:
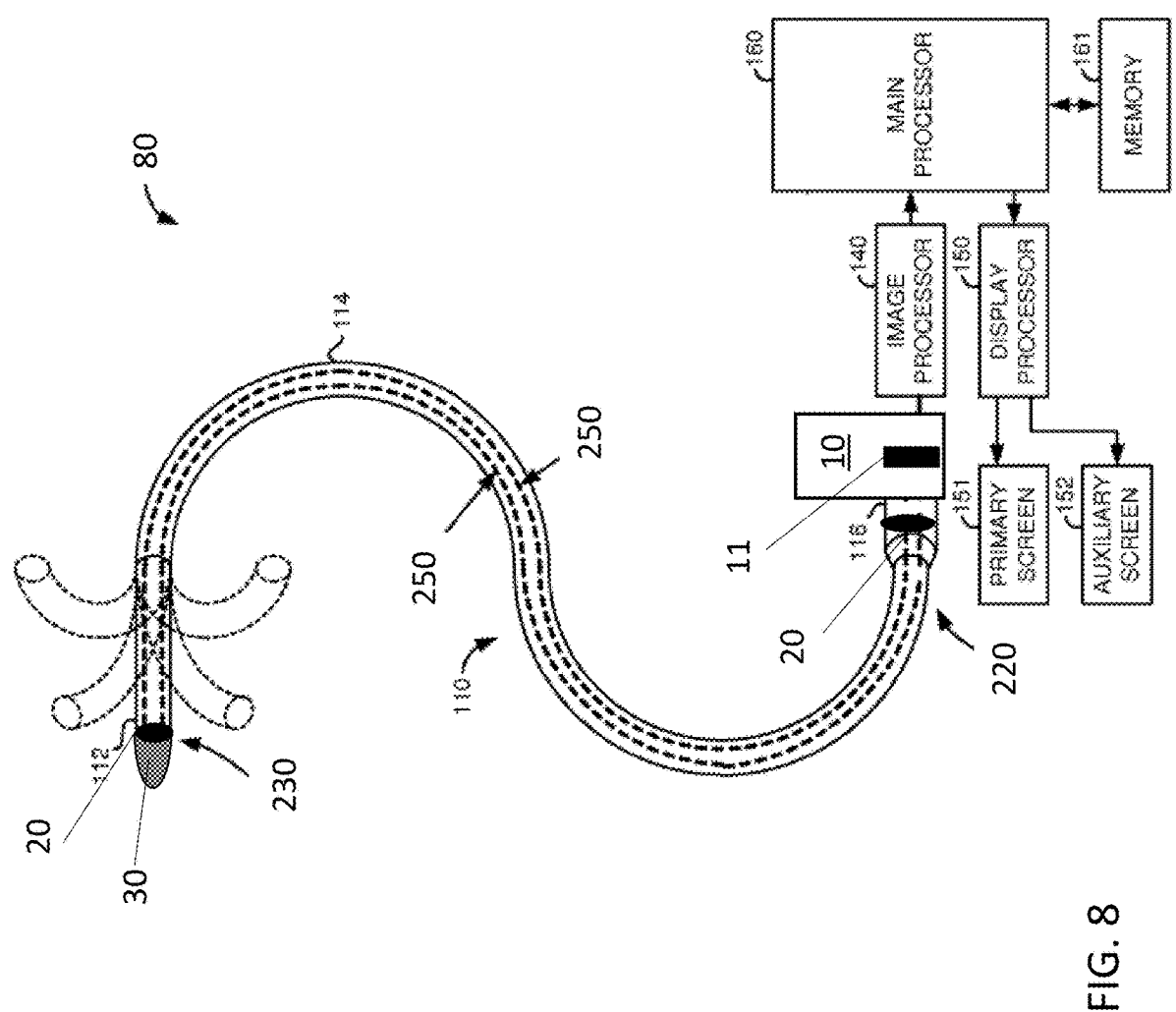
FIG. 8 is a block diagram of an example of a steerable plenoptic endoscope system.

FIG. 8 illustrates, as an example, a plenoptic endoscope 80 including a steerable fiber bundle 110, a plenoptic camera system 10 with an image sensor 11, an image processor 140 coupled to the plenoptic camera system 10, a plurality of fiber optic strands 250 directing light from an objective lens 30 at the distal end 230 of the steerable fiber bundle 110 to the image sensor 11, a display processor 150, a primary display screen 151, an auxiliary display screen 152, a main processor 160, and memory 161. Although shown as separate units, the image processor 140, display processor 150, and main processor 160 may be implemented in a single processor or their respective functions distributed among a plurality of processors, where each of such processors may be implemented as hardware, firmware, software or a combination thereof. As used herein, the term processor is understood to include interface logic and/or circuitry for translating and/or communicating signals into and/or out of the processor as well as conventional digital processing logic. The memory 161 may be any memory device or data storage system as conventionally used in computer systems. The primary and auxiliary display screens, 151 and 152, are preferably computer monitors capable of displaying three-dimensional images to an operator of the plenoptic endoscope 80. However, for cost or other considerations, either or both of the primary and auxiliary display screens, 151 and 152, may be a standard computer monitor capable of only displaying two-dimensional images.

The steerable fiber bundle 110 has a flexible body 114, a steerable tip 112 at its distal end 230, and a hand-operable handle 116 at its proximal end 115. Control cables (not shown) or other control means typically extend from the handle 116 to the steerable tip 112 so that the tip 112 may be controllably bent or turned as shown for example by dotted line versions of the bent tip 112.

The image sensor 11 of the plenoptic camera system 10 outputs image data to be processed by the image processor 140 and/or display processor 150 and displayed on the primary display screen 151, auxiliary display screen 152, and/or other display means according to the various aspects of the invention as described herein. The plenoptic camera system 10 may also be single or multi-spectral that captures image data in the visible or infrared/ultraviolet spectrum. Thus, any image sensor 11 referred to herein may be any one or a combination of these and other imaging technologies. In some implementations, a portion of an image sensor can be configured to sense light in a first portion of the spectrum (e.g., visible light range) while another portion of the sensor is configured to sense light in a different, second portion (e.g., infra-red) that is at least partially non-overlapping with the first portion. One of a plurality of fiber optic strands 250 may be coupled at its sensor end 220 to a light source (not shown) for illumination purposes at the distal end 230. Another of the plurality of fiber optic strands 250 may be configured with position and bend or shape sensors such as Fiber Bragg Gratings (or other strain sensors such as those employing Rayleigh scattering) distributed along the length of the steerable fiber bundle 110 so that light passing through these fiber optic strands 250 are processed by a sensor processor (not illustrated) to determine a current pose and shape of the steerable fiber bundle 110.

Figure 9:
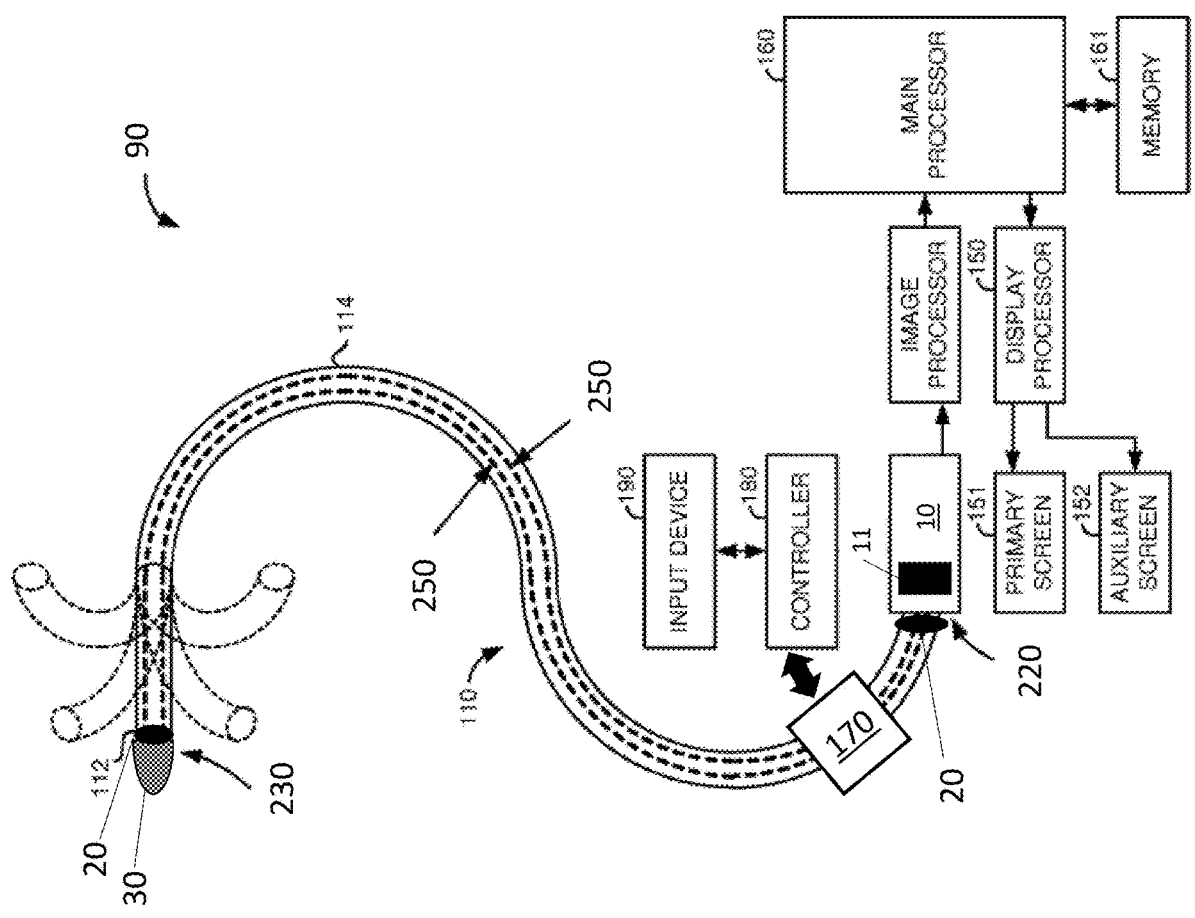
FIG. 9 is a block diagram of a remotely operated steerable plenoptic endoscope system.

FIG. 9 illustrates, as an example, an alternative embodiment of the plenoptic endoscope 90 in which the handle 116 is replaced by an electromechanical interface 170, controller 180, and input device 190 for teleoperating the steerable fiber bundle 110 of the plenoptic endoscope 90. The interface 170 includes actuators for actuating cables in the steerable fiber bundle 110 to steer its tip 112 as well as an actuator for moving the entire steerable fiber bundle 110 forward and backward so that it may be inserted into and retracted out of a patient through an entry port such as a natural body orifice or a surgeon created minimally invasive incision. In addition, the interface 170 may include an actuator for rotating the steerable fiber bundle 110 about its central longitudinal axis. The controller 180 is preferably implemented as hardware, firmware or software (or a combination thereof) in the same one or more computer processors as the processors 140, 150, and 160, or a different computer processor. The flexible body 114 may be passively or actively bendable. The plenoptic endoscope 90 can also be a hybrid of the above two examples.

The functionality described herein, or portions thereof, and its various modifications (hereinafter "the functions") can be implemented, at least in part, via a computer program product, e.g., a computer program tangibly embodied in an information carrier, such as one or more non-transitory machine-readable media or storage device, for execution by, or to control the operation of, one or more data processing apparatus, e.g., a programmable processor, a DSP, a microcontroller, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed one or more processing devices at one site or distributed across multiple actions associated with implementing all or part of the functions can be performed by one or more programmable processors or processing devices executing one or more computer programs to perform the functions of the processes described herein. All or part of the functions can be implemented as, special purpose logic circuitry, e.g., an FPGA, an ASIC (application-specific integrated circuit), GPU (graphics processing unit), a Tensor Processing Unit (TPU), and/or another parallel processing unit.

Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous, for example, in image reconstruction. Moreover, the separation of various system modules and components in the embodiments described herein should not be understood as requiring such separation in all embodiments, and it should be understood that the described program components and systems can generally be integrated together in a single product or packaged into multiple products.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A plenoptic endoscope, comprising:
 a fiber bundle comprising:
  a distal end configured to receive light from a target imaging region,
  a sensor end disposed opposite the distal end, and
  a plurality of fiber optic strands each extending from the distal end to the sensor end;
 an image sensor coupled to the sensor end of the fiber bundle; and
 a plurality of microlenses disposed between the image sensor and the sensor end of the fiber bundle, the plurality of microlenses forming an array that receives light from one or more of the plurality of fiber optic strands of the fiber bundle and directs the light received from the one or more of the plurality of fiber optic strands of the fiber bundle onto the image sensor, wherein the plurality of microlenses and the image sensor together form a plenoptic camera configured to capture information about a light field emanating from the target imaging region.

2. The plenoptic endoscope of claim 1, comprising a main lens assembly arranged at the distal end of the fiber bundle, the main lens assembly arranged to direct the light from the target imaging region through the plurality of fiber optic strands.

3. The plenoptic endoscope of claim 2, wherein the main lens assembly comprises an objective lens defining a field of view of the light directed from the target imaging region through the plurality of fiber optic strands.

4. The plenoptic endoscope of claim 1, wherein the fiber bundle is flexible.

5. The plenoptic endoscope of claim 1, wherein the fiber bundle comprises a proximal portion and a distal portion coupled at a joint along a length of the fiber bundle, the joint enabling angular movement of the distal portion with respect to the proximal portion about the joint.

6. The plenoptic endoscope of claim 5, wherein the joint comprises an electric motor configured to cause the angular movement of the distal portion with respect to the proximal portion about the joint.

7. The plenoptic endoscope of claim 1, wherein the fiber bundle comprises a plurality of separate, individually flexible arms, each of the plurality of flexible arms comprising a subset of the plurality of fiber optic strands.

8. The plenoptic endoscope of claim 7, wherein the image sensor comprises a plurality of image sensing regions, wherein each image sensing region of the plurality of image sensing regions is arranged to receive light from one of the plurality of flexible arms.

9. The plenoptic endoscope of claim 8, wherein a first image sensing region of the plurality of image sensing regions is configured to sense at least a first range of wavelengths of light, and wherein a second image sensing region is configured to sense at least a second range of wavelength of light, the first range and the second range being at least partially non-overlapping.

10. The plenoptic endoscope of claim 9, wherein the first image sensing region is configured to sense visible light, and wherein the second image sensing region is configured to sense infrared light.

11. The plenoptic endoscope of claim 7, comprising at least one light source, wherein the subset of the plurality of fiber optic strands of each flexible arm of the plurality of flexible arms forms a light guide arranged to direct light from the at least one light source to a distal end of each flexible arm of the plurality of flexible arms to illuminate at least a portion of the target imaging region, wherein a first optical filter disposed at the distal end of a first flexible arm of the plurality of flexible arms is configured to pass light in a first wavelength range, and wherein a second optical filter disposed at the distal end of a second flexible arm of the plurality of flexible arms is configured to pass light in a second wavelength range that is at least partially non-overlapping with the first wavelength range.

12. The plenoptic endoscope of claim 7, wherein the image sensor comprises a plurality of pixel arrays, wherein each pixel array of the plurality of pixel arrays is arranged to receive light from one of the plurality of flexible arms.

13. The plenoptic endoscope of claim 1, wherein the fiber bundle is configured to be inserted into an animal or human body.

14. The plenoptic endoscope of claim 1, comprising at least one light source, and wherein a subset of the plurality of fiber optic strands forms a light guide arranged to direct light from the at least one light source to the distal end of the fiber bundle to illuminate the target imaging region.

15. The plenoptic endoscope of claim 1, wherein each of the plurality of microlenses is arranged to receive light from at least one of the plurality of fiber optic strands of the fiber bundle and to direct the light from the at least one of the plurality of fiber optic strands of the fiber bundle onto the image sensor.

16. The plenoptic endoscope of claim 1, wherein one or more of the plurality of microlenses is arranged to receive light from one of the plurality of fiber optic strands of the fiber bundle and direct the light from the one of the plurality of fiber optic strands of the fiber bundle onto the image sensor.

17. The plenoptic endoscope of claim 1, further comprising one or more processing devices operatively coupled with the image sensor and configured to calculate surface image data for a surface in the target imaging region.

18. The plenoptic endoscope of claim 17, where the one or more processing devices is configured to generate representations of a depth map based on the surface image data and a photographic image.

* * * * *